United States Patent [19]
Boillot

[11] 3,949,590
[45] Apr. 13, 1976

[54] METHOD AND APPARATUS FOR MEASURING GASES IN A METAL SAMPLE

[75] Inventor: Pierre Boillot, Le Pecq, France

[73] Assignee: Institut de Recherches de la Siderurgie Francaise (IRSID), Saint Germain en Laye, France

[22] Filed: Aug. 7, 1972

[21] Appl. No.: 278,560

[30] Foreign Application Priority Data
Aug. 12, 1971 France .............................. 71.29506

[52] U.S. Cl. .................................................. 73/19
[51] Int. Cl.² ......................................... G01N 7/16
[58] Field of Search ............... 73/19, 23.1, 27 R, 23

[56] References Cited
UNITED STATES PATENTS

| | | | |
|---|---|---|---|
| 2,729,969 | 1/1956 | Innes .................................. | 73/19 X |
| 2,861,450 | 11/1958 | Ransley ................................ | 73/19 |
| 3,159,020 | 12/1964 | Donner et al. ....................... | 73/23.1 |
| 3,286,530 | 11/1966 | Ayers .................................. | 73/19 X |
| 3,427,863 | 2/1969 | Schultz ................................ | 73/19 X |
| 3,633,616 | 1/1972 | Meshek ............................... | 73/23.1 X |

FOREIGN PATENTS OR APPLICATIONS
688,927  10/1966  Belgium ................................. 73/19

OTHER PUBLICATIONS
*Vapor Fractometry (Gas Chromatography),* H. H. Hausdorff, The Perkin–Elmer Corp., p. 22, 6-24-58.

*Primary Examiner*—Richard C. Queisser
*Assistant Examiner*—Stephen A. Kreitman
*Attorney, Agent, or Firm*—Burgess Ryan and Wayne

[57] ABSTRACT

Method and apparatus for measuring the gas in a metal sample wherein a reference circuit has gas flowed therethrough from a source, a detection circuit including a degassing chamber therein has gas flowed therethrough from the same source, the reference and detection circuits leading to comparison cells of a catharometer and then to a common measuring circuit, and a complementary circuit is connected to the detection circuit with a gas flow therethrough to selectively apply a protective gas curtain to the degassing chamber during introduction and removal of the sample.

5 Claims, 4 Drawing Figures

METHOD AND APPARATUS FOR MEASURING GASES IN A METAL SAMPLE

The present invention relates to the determination of the quantity of gaseous element in a metal sample.

It is well known that the gases present in a solid metal, such as steel, have a considerable influence on some of the physical and mechanical characteristics of the metal. Accordingly attempts have been made, in correspondence with metallurgical treatments undertaken for the purpose of lowering the content of residual gases in the metals, to find methods of analysis by which it is possible to determine with increasing accuracy smaller and smaller quantities of gas.

Hydrogen in the residual state is the most prejudicial gas as far as concerns the alteration in the properties of metals. In the following discussion, hydrogen will be referred to generally, but it will be appreciated that the same principles are also true for other gases present in solid metals.

Standard methods are known, for instance, which make use of extraction, under vacuum or under argon, of the hydrogen of a solid sample of heated metal, and the separation of other gases released at the same time as the hydrogen by the passage of the gaseous mixture a palladium filter. The diffused hydrogen is then evaluated by volumetric or electrical measurement. The time required for carrying out the analyses by this method is too long (at least 30 minutes) to enable checking to be made in the course of the working-up treatment.

Other analysis methods use chromatography to separate the various gases, followed by a suitable measurement operation. These methods may be used whatever may be the method of extraction of the gases either in solid or liquid state. The released gases are carried away by vacuum or by flowing through an inert gas, known as the carrier gas, towards separation and detection devices, most frequently with thermal conductivity devices for hydrogen and nitrogen and infra-red devices for carbon monoxide The carrier gas, which is generally argon or helium, carries along the gases extracted from the sample in varying quantities and of varying nature according to the heating or melting method used. Certain of these constituents interfere with the hydrogen so that steps are taken to separate, delay or absorb them. On the registering device there is plotted a series of peaks corresponding to the successive passage of the different gases.

It is known that the disadvantages of separation columns are principally of masking the kinetics of gaseous releases and of imposing rigorously programmed operating methods. This technique will be gone into in greater detail in the description which follows.

The aim of the invention is to provide a method of analysis and an apparatus for carrying out the method, by which it is possible to determine the hydrogen in metals and in particular in steel, with brief analysis times and a high degree of accuracy.

The invention provides a method of determining the quantity of a gaseous element in a metal sample in which the sample is heated in a degassing chamber, the released gases are carried along by a carrier gas into a detection circuit and the unbalance of a catharometric bridge is detected, the bridge having two cells through which pass respectively gases coming from the detection circuit and a current of the carrier gas coming from a reference circuit. The detection and reference circuit are supplied in parallel from a common source of carrier gas. The carrier gas is drawn through the circuits by a common pump. The pump draws equal and constant flows of gas through the circuits, the sum of these flows being less than the flow supplied by the source of carrier gas, the supply pressure being kept practically equal to the external pressure at a junction point of the source of carrier gas and the two circuits by means of a vent through which excess carrier gas escapes. A surplus of carrier gas is supplied to form a curtain of protective gas which isolates the degassing chamber from the atmosphere when it is opened for the introduction or removal of the sample.

When the release of the gaseous element to be determined is accompanied by the release of another gas tending to disturb the catharometric measurement, the carrier gas may be the same gas as the gas causing the disturbance. If hydrogen is the gas, the quantity of which is being measured, nitrogen may be used as the carrier gas because the release of hydrogen is accompanied by a release of nitrogen which disturbs the measurement operation.

When the content in carbon monoxide is considered to be sufficiently large to disturb any analysis being undertaken, for instance in the case in which the sample is placed in a graphite crucible brought to a high temperature and according to its oxygen content, the gas is trapped in a known manner.

The invention also provides apparatus for determining the quantity of a gaseous element in a metal sample, comprising: a source of carrier gas which supplies in parallel, through a first control valve for the flow which includes a vent to the exterior, a reference circuit and a detection circuit both terminating in a common third circuit composed of a first pressure drop element and a suction pump. The reference circuit comprises successively a second pressure drop element and a first cell of a catharometer, and the detection circuit comprises successively a first opening and closing valve, a degassing chamber provided with means for heating the sample, a third pressure drop element and a second cell of the catharometer. The degassing chamber has an orifice for the introduction of the sample provided with means known per se for flowing in gas to form a gaseous curtain isolating the interior of the chamber from the atmosphere, the gas forming the curtain being part of the carrier gas. A complementary circuit having in series a second opening and closing valve and a second control valve for the rate of flow supplies a surplus of carrier gas from the said source to the flowing-in means of the orifice of the degassing chamber, when the orifice is open.

The orifice of the degassing chamber is preferably provided with opening or closing means which control simultaneously, respectively, the closing or opening of the first valve in the detection circuit and the opening or closing of the second valve in the complementary circuit. These valves may be electrically operated valves controlled by an electrical contact actuated by the opening or closing means for the orifice of the degassing chamber.

The reference and detection circuits may be brought to the same temperature by heat exchangers through which a common fluid flows, for instance, cooling fluid of the degassing chamber.

The invention is further described below with reference to the accompanying drawings, in which.

Figure 1:
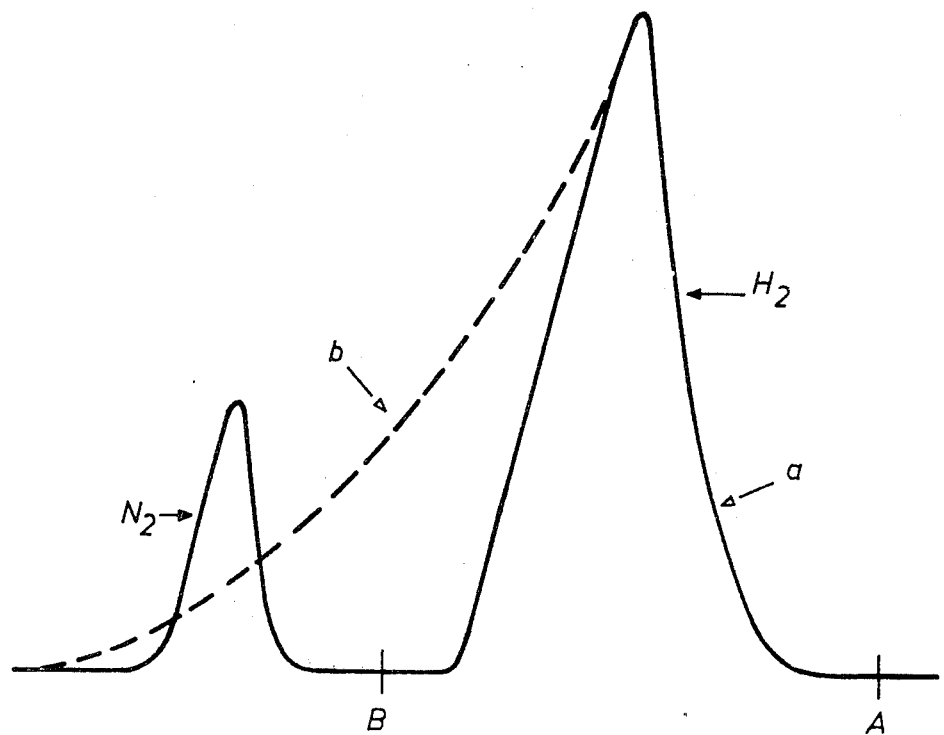
FIG. 1 shows an analysis graph obtained by chromatography.

In the known method of carburizing melting utilizing chromatography, there is collected a gaseous mixture containing, a carrier gas, argon or helium, hydrogen, nitrogen and carbon monoxide formed from the oxygen contained in the metal. The carrier gas flows through the reference circuit itself. The plotting effected at the terminals of a detection bridge records unbalance due to the presence of nitrogen, hydrogen and carbon monoxide. The presence of nitrogen which interferes with the measurement of the hydrogen necessitates the separation of the nitrogen and the hydrogen, obtained as has been stated, by slowing down the passage of the nitrogen in relation to the hydrogen by means of columns filled with molecular sieves. Accordingly, in favorable conditions, two separate peaks are obtained, which are shown by line $a$ in FIG. 1. It can be seen that by integrating the hydrogen peak between A and B one can evaluate the quantity of hydrogen present in the sample. The integration must of necessity be effective within these limits so as not to take into account the nitrogen, the peak of which follows that of the hydrogen. Moreover it frequently happens that the release of hydrogen is much slower, accordingly more spread out in time as a result of the presence in the metal of compounds such as hydrates. The peak corresponding to the hydrogen is then much more spread out, as shown by line $b$ in FIG. 1, and it can be seen that a limited integration between A and B no longer allows the total amount of released hydrogen to be evaluated, so that faulty analyses are obtained. In practice, a form of peak corresponding line $b$ is met with far more often than that of line $a$.

Rather than carry out unreliable separations which do not give satisfaction in all circumstances the inventor has considered the problem from a quite different aspect and according to the idea given below.

Figure 2:
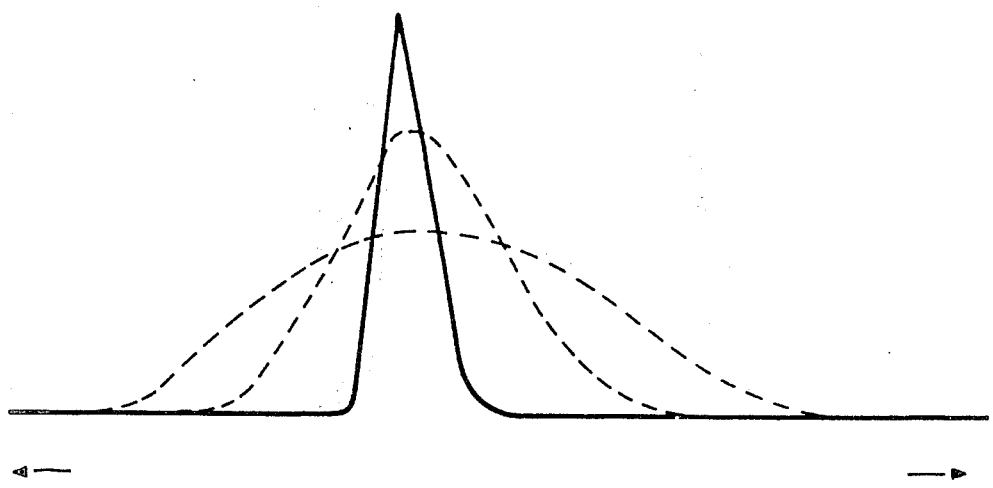
FIG. 2 shows an analysis graph obtained by the use of the invention.

Since a detection by differential measurement of thermal conductivity between a gaseous reference current and the gaseous analysis current is being carried out, the absolute conductivity of the reference mixture is of little importance, the important thing being to emphasize the difference in conductivity due to the hydrogen. The element causing the most trouble in evaluating the hydrogen is, as has been seen, nitrogen. The inventor has accordingly decided to use as a carrier gas the gas which is itself the disturbing element. By this fact in the present invention the reference circuit and the detection circuit have a considerable flow of nitrogen passing through them. In the absence of any other gas no unbalance of the bridge is recorded. It can easily be conceived that the quantities of nitrogen supplied by the sample are absolutely negligible and cannot contribute to modify the rate of flow as to cause unbalancing of the measurement bridge. The plotting thus obtained now shows only one peak corresponding to the unbalance provided by the hydrogen (FIG. 2) from which is obtained the possibility in integration over considerable time, which makes it possible to measure the area of the peak whatever may be its spread. Moreover, one is freed totally from molecular sieve columns and the uncertainty which they bring with them. Of course this idea can be applied in a very general manner.

If one considers the case of carbon monoxide, this is found to be not very troublesome in small quantities, since its thermal conductivity is approximately one seventh that of hydrogen. Nevertheless if it is found to be necessary it is very easy to trap it continuously by chemical reaction in a known manner before detection.

Figure 3:
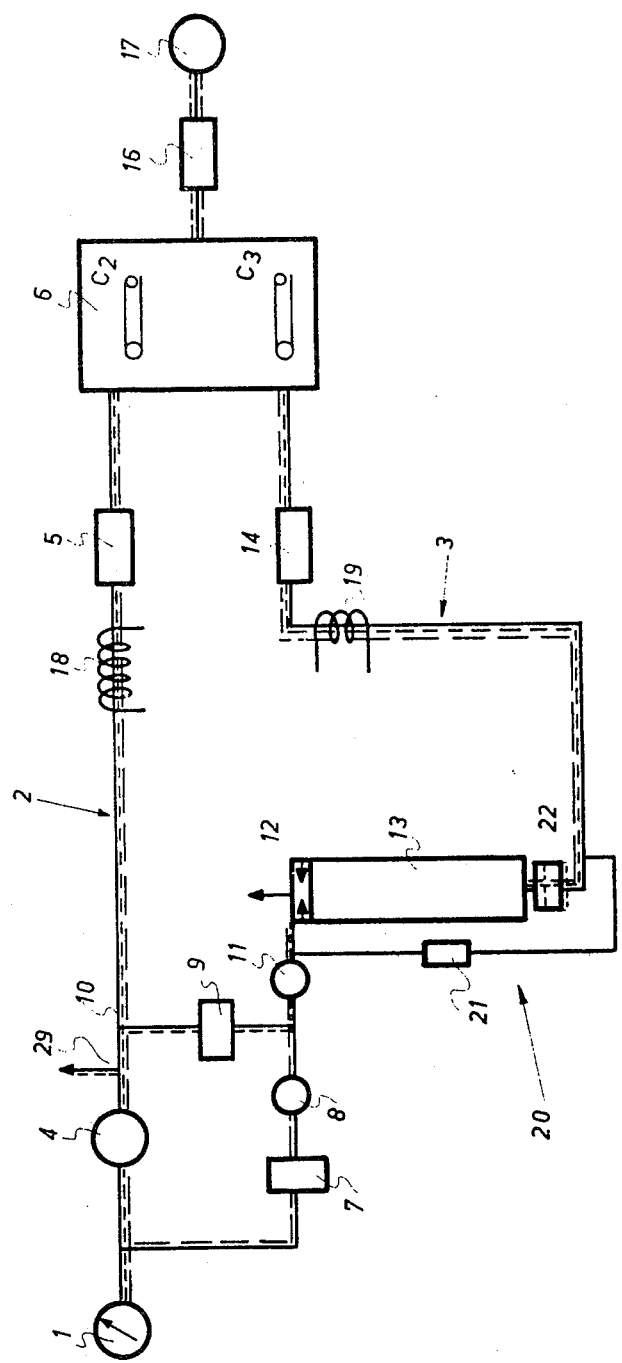
FIG. 3 shows diagrammatically an apparatus according to the invention.

The apparatus shown in FIG. 3 comprises a source of carrier gas at atmospheric pressure having a container 1 for the gas under pressure, a valve in the form of a regulating tap 4 for the rate of flow and a vent 29 into the atmosphere. From this source two branch circuits 2 and 3 extend. The circuit 2 is a reference circuit. The circuit 2 includes a pressure drop member constituted by a calibrated capillary 5 and a first cell $C_2$ of a standard catharometer 6. The circuit 3 is a detection circuit. The circuit 3 includes an electrically operated valve 9, a degassing chamber 13, a pressure drop member constituted by a calibrated capillary 14, and a second cell $C_3$ of the catharometer 6.

The degassing chamber 13 is provided with an injection device 12 at its end through which the samples are introduced. By the device 12, it is possible to provide a curtain of protective gas which isolates the chamber 13 from the atmosphere when the chamber is open. The chamber is moreover provided with a heating inductor, not shown, for heating the sample and a crucible which contains it. The degassing chamber is not described in great detail and may be of known type or a new development.

Between the valve 9 and the chamber 13, a device 11 is mounted by which it is possible to introduce predetermined volumes of gas in order to calibrate the apparatus.

On issuing from the catharometer, the two gaseous currents are picked up by a single circuit 15 having a pressure drop element constituted by a capillary 16 and a pump 17 with a constant rate of flow. In order to avoid any accidental unbalance of the bridge by reason of stray currents, the circuits 2 and 3 are kept at the same temperature by coils 18 and 19 fed by the cooling fluid of the induction furnace of the degassing chamber. A branch circuit 20 having two electrically operating valves 21 and 22 enables the chamber 13 to be isolated without interrupting the gaseous flow, thus enabling maintenance operations to be undertaken without loss of thermal equilibrium of the whole system, in particular of the catharometer, which takes a long time to set up.

A complementary circuit having an electrically operated valve 7 and a valve in the form of a regulating tap 8 extends from the gas container 1 and ends in the detection circuit upstream of the injection device 12. The complementary circuit is for providing a surplus of carrier gas to supply a curtain of gas when the chamber 13 is opened for the introduction of the sample or the changing of the crucible.

Figure 4:
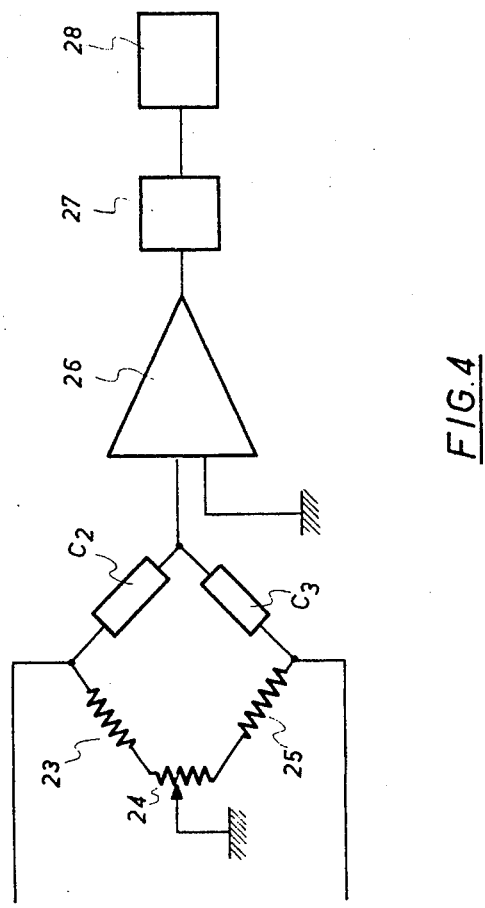
FIG. 4 shows a diagram of an integration device of the apparatus shown in FIG. 3.

Integration equipment is associated with the catharometer and enables the measurement of the area of the $H_2$ peak obtained to be made, such area being proportional to the quantity of gas as is known. The measurement consists in detecting the direct unbalance voltage of a Wheatstone bridge, two branches of which are constituted by the two cells $C_2$ and $C_3$ of the catharometer as can be seen in FIG. 4, through which pass respectively the reference current and the gas detection current; the other two branches being constituted by three resistances 23, 24, 25, the resistance 24 being a variable resistance. The bridge is initially balanced by means of the resistance 24 and any subsequent unbalance of the bridge due to a change in composition of the gas in cell $C_3$ causes the occurrence of a direct voltage U in the horizontal diagonal of the bridge. This voltage is then raised to a suitable level by an operational amplifier 26. The measurement device includes a voltage frequency converter 27 and an integration device with numerical posting up 28, which adds up the pulses emitted by the converter 27 and supplies the integral of the unbalance voltage for the duration of the analysis. The reading sensitivity reaches 0.01ppm. In order to be able to see the curve visually, a recorder may be connected at the output of the operational amplifier 26.

The operation of the apparatus will now be described with reference to FIG. 3. Taking the capillaries 5, 14, 16 and a pump selected to obtain in the circuits 2 and 3 a rate of flow of 10 liters per hour, which consequently results in a rate of flow of 20 liters per hour through the capillary 16 and the pump 17, a rate of flow supplied by the source 1 at a higher value, 30 litres per hour, for instance, if provided. When the chamber 13 is closed, the valve 7 is closed and the valve 9 is open, the nitrogen spreads between the two circuits following the paths shown in short dotted lines. By the presence of the capillaries 5, 14, 16 and the rate of flow of the pump, the two circuits have passing through them a uniform rate of flow of 10 litres per hour. The excess nitrogen escapes freely to the atmosphere through the vent 29. The chamber 13 is opened, and this act of opening brings about, by a suitable device, which in the present example is an electrical contact, the opening of the valve 7 and the closing of the valve 9.

The gas then follows the path shown in long dotted lines in FIG. 3. Accordingly, it can be seen that the device 12 is supplied with a curtain of nitrogen that forms at the entry of the chamber 13 isolating it from the atmosphere. The excess nitrogen escapes and in this case the chamber still remains at atmospheric pressure. It is accordingly possible to introduce the sample without bringing about the entry of air which would falsify the results. It will accordingly be noted that the rates of flow of gas in the cells of the catharometer remain identical all the time whatever operation may be taking place and that the pressure in the degassing chamber is always atmospheric pressure.

The method of the invention, besides having great simplicity and requiring only simple apparatus for its putting into effect, has numerous advantages.

In actual fact it does not require any separation of the elements and accordingly it is unnecessary to use molecular sieves, the use of which is always a risky matter. Moreover, the possibility of doing without molecular sieves enables the kinetics of the release of gases to be followed, which has great interest for the study of mechanisms of gaseous release. From this fact all the analysis circuits are reduced to the minimum which is always preferable when one is working with gases and makes it possible to obtain measurement times which are very much smaller, of the order of 1 minute 30 seconds. Another important advantage is the suppression of air lock chamber entry as a result of the isolation of the chamber by the gaseous curtain. In actual fact in the course of its stay in such an air lock the sample begins to release gases which in the prior art escape the analysis operation. With the apparatus described, as soon as the sample has been introduced into the chamber and even if the chamber is still not closed, the gas which is released is carried along by the current of nitrogen and taken into account for analysis. Another advantage of the curtain of gas is the absence of pressure shock which is translated by the appearance of a parasitic peak at the output of the catharometer at the moment of the introduction of the sample, as is inevitably produced with other methods.

According to measurement requirements, work can be undertaken as described by carburizing fusion of the sample in a graphite crucible or simply by heating the sample in the solid phase. It will also be noted that the idea of the apparatus makes it possible to effect calibration or adjustment under the actual conditions of the analysis, that is to say in the presence of a crucible and a sample of metal free of hydrogen.

It is also an important advantage that the whole of the gas withdrawn is analyzed and that is is possible to integrate the entire area of the peak however spread out it may be.

Finally, the gases are extracted or pumped and not propelled as in conventional methods, which makes it possible to detect immediately the existence of any leak in the circuits.

Thus the apparatus described above provides rapid and accurate measurements, and is particularly well adapted for measuring the content of the hydrogen in metals during various stages of the treatment of the metals. The invention is particularly suitable for measuring the amount of hydrogen in steel so that the quality of the steel can be controlled.

With a suitable choice of carrier gas, the invention is applicable to the determination of the quantities of gases other than hydrogen in metals.

What I claim is:

1. An apparatus for determining the quantity of a gaseous element in a metal sample, comprising: a source of carrier gas including means for controlling the rate of flow of carrier gas from the source, and means for controlling a positive pressure on the carrier gas slightly above atmospheric pressure; a reference circuit; a detection circuit, and a third circuit; said reference circuit and said detection circuit being connected in parallel between the source of carrier gas and said third circuit; said third circuit including a suction means and a first flow control means, the reference circuit including a second flow control means and a first cell of a catharometer, the detection circuit including a first valve means, a degassing chamber, and a third flow control means and a second cell of the catharometer, the degassing chamber being provided with means for heating the sample therein and further having means for introducing and removing the sample; a complementary circuit connected to said source of carrier gas including a second valve means and means for forming a gaseous curtain for isolating the degassing chamber from the atmosphere during introduction and removal of the sample.

2. An apparatus according to claim 1, wherein said degassing chamber has an opening for the introduction and removal of the sample, and means are provided for opening or closing the opening of the degassing chamber which also controls the opening or closing of said first valve means in the detection circuit and the opening or closing of said second valve means in the complementary circuit.

3. An apparatus according to claim 2, wherein said first valve means in the detection circuit and said second valve means in the complementary circuit are electrically operated valves controlled by an electric contact actuated by said means for opening or closing the opening of the degassing chamber.

4. A method of measuring the quantity of a gaseous element in a sample, comprising:

simultaneously supplying a reference circuit and a detection circuit with a first current of carrier gas and a second current of carrier gas, respectively, both currents of carrier gas being supplied from a common source of carrier gas;

maintaining the pressure of the carrier gas supplied by said source equal to external pressure by supplying a rate of flow of carrier gas in excess of the rate of flow needed by the first and the second currents and by continuously venting excess gas;

at the same time heating the sample in a degassing chamber forming part of the detection circuit to release the gaseous element therefrom;

at the same time drawing by means of a common suction pump the first current of carrier gas through the first cell of a catharometric bridge inserted in said reference circuit and the second current of carrier gas through the degassing chamber and thence, together with the gaseous element released from the sample, through a second cell of the catharometric bridge inserted in said detection circuit;

continuously maintaining the rate of flow of the first current of carrier gas through the first cell of the catharometric bridge substantially equal to the rate of flow of the second current of carrier gas through the degassing chamber and the second cell of the catharometric bridge;

at the same time detecting any unbalance of the catharometric bridge; and supplying excess carrier gas to the degassing chamber to form a gaseous curtain when the degassing chamber is opened to introduce or remove the sample.

5. A method according to claim 4, wherein the gaseous element is hydrogen and the carrier gas is nitrogen.

* * * * *